(12) United States Patent
Serban et al.

(10) Patent No.: US 12,319,880 B2
(45) Date of Patent: Jun. 3, 2025

(54) PROCESS FOR CONVERTING OLEFINS TO DISTILLATE FUELS WITH REGENERATION

(71) Applicant: UOP LLC, Des Plaines, IL (US)

(72) Inventors: Manuela Serban, Northbrook, IL (US); Deng-Yang Jan, Elk Grove Village, IL (US); Ashish Mathur, Gurgaon (IN); Joseph A. Montalbano, Bradenton, FL (US); Christopher Procopi, Glencoe, IL (US); Erick J. Bennett, III, New Lenox, IL (US); Jeannie Mee Blommel, Oregon, WI (US)

(73) Assignee: UOP LLC, Rosemont, IL (US)

( * ) Notice: Subject to any disclaimer, the term of this patent is extended or adjusted under 35 U.S.C. 154(b) by 0 days.

(21) Appl. No.: 18/238,964

(22) Filed: Aug. 28, 2023

(65) Prior Publication Data
US 2025/0075134 A1   Mar. 6, 2025

(30) Foreign Application Priority Data
Aug. 30, 2022   (IN) .............................. 202211049525

(51) Int. Cl.
*C10G 65/00* (2006.01)
*C10G 65/04* (2006.01)

(52) U.S. Cl.
CPC ....... *C10G 65/043* (2013.01); *C10G 2400/08* (2013.01); *C10G 2400/22* (2013.01)

(58) Field of Classification Search
CPC .............. C10G 65/043; C10G 2400/08; C10G 2400/22
See application file for complete search history.

(56) References Cited

U.S. PATENT DOCUMENTS

| | | | |
|---|---|---|---|
| 9,550,705 B2 | 1/2017 | Tosin et al. | |
| 9,932,531 B2 | 4/2018 | Lilga et al. | |
| 9,957,449 B2 * | 5/2018 | Luebke | ..................... C10L 1/04 |
| 2016/0312131 A1 | 10/2016 | Luebke et al. | |
| 2018/0155637 A1 | 6/2018 | McCarthy et al. | |
| 2021/0207039 A1 | 7/2021 | Dharia et al. | |

FOREIGN PATENT DOCUMENTS

WO   WO-2016067033 A1 *   5/2016   .............. B01J 21/04

OTHER PUBLICATIONS

Search Report and Written Opinion for PCT/US2023/073180 dated Dec. 8, 2023.

* cited by examiner

*Primary Examiner* — Ellen M McAvoy
*Assistant Examiner* — Chantel Graham
(74) *Attorney, Agent, or Firm* — Paschall & Associates, LLC.; James C. Paschall (57) ABSTRACT

A process for oligomerizing and oligomerizing olefins to distillate fuels which regenerates a first stage oligomerization catalyst bed and/or a second oligomerization catalyst bed in situ by contact with an oxygen gas at elevated temperature. The oligomerization catalyst can be restored to full activity. A regeneration process can enable continuous operation.

20 Claims, 6 Drawing Sheets

| Reactors | Week--> | 1 | 2 | 3 | 4 | 5 | 6 | 7 | 8 | 9 | 10 | 11 | 12 |
|---|---|---|---|---|---|---|---|---|---|---|---|---|---|
| | | <---------------------------------- Regeneration System ----------------------------------> | | | | | | | | | | | |
| 1st Stage Oligomerization Reactor 22a | | Lead | Lead | Lag | Lag | Regen + Idle | Idle | Lead | Lead | Lag | Lag | Regen + Idle | Idle |
| 1st Stage Oligomerization Reactor 22b | | Lead | Lead | Lag | Lag | Regen + Idle | Idle | Lead | Lead | Lag | Lag | Regen + Idle | Idle |
| | | <---------------------------------- 1st Stage Oligomerization Full Cycle ----------------------------------> | | | | | | | | | | | |
| 1st Stage Oligomerization Reactor 22c | | Lag | Lag | Regen + Idle | Idle | Lead | Lead | Lag | Lag | Regen + Idle | Idle | Lead | Lead |
| 1st Stage Oligomerization Reactor 22d | | Lag | Lag | Regen + Idle | Idle | Lead | Lead | Lag | Lag | Regen + Idle | Idle | Lead | Lead |
| 1st Stage Oligomerization Reactor 22e | | Regen + Idle | Idle | Lead | Lead | Lag | Lag | Regen + Idle | Idle | Lead | Lead | Lag | Lag |
| 1st Stage Oligomerization Reactor 22f | | Regen + Idle | Idle | Lead | Lead | Lag | Lag | Regen + Idle | Idle | Lead | Lead | Lag | Lag |
| | | | | | | | <---------------------------------- 2nd Stage Oligomerization Full Cycle ----------------------------------> | | | | | | |
| 2nd Stage Oligomerization Reactor 32a | | Lead | Lag | Lag | Regen + Idle | Idle | Lead | Lead | Lag | Lag | Regen + Idle | Idle | Lead |
| 2nd Stage Oligomerization Reactor 32b | | Lag | Regen + Idle | Idle | Lead | Lead | Lag | Lag | Regen + Idle | Idle | Lead | Lead | Lag |
| 2nd Stage Oligomerization Reactor 32c | | Idle | Lead | Lead | Lag | Lag | Regen + Idle | Idle | Lead | Lead | Lag | Lag | Regen + Idle |

PROCESS FOR CONVERTING OLEFINS TO DISTILLATE FUELS WITH REGENERATION

CROSS-REFERENCE TO RELATED APPLICATIONS

This application claims priority from Indian Provisional Patent Application No. 202211049525, filed Aug. 30, 2022, which is incorporated herein in its entirety.

FIELD

The field is the conversion of olefins to distillate. The field may particularly relate to oligomerizing olefins and oligomerizing the oligomerized olefins to distillate fuels.

BACKGROUND

Ethylene can be dimerized into olefins such as C4, C6 and C8 olefins. Olefin oligomerization is a process that can oligomerize smaller olefins into larger olefins. More specifically, it can convert olefins including dimerized olefins into distillates including jet fuel and diesel range products. The oligomerized distillate can be saturated for use as transportation fuels.

The dimerization reaction of ethylene is highly exothermic. The exotherm generated by ethylene dimerization can be difficult to manage.

Jet fuel is one of the few petroleum fuels that cannot be replaced easily by electrical motor systems because a high energy output is required to fuel planes which cannot be supplied with electric motors. Large incentives are currently available for green jet fuel in certain regions.

An efficient process is desired for converting ethylene to distillate fuels.

BRIEF SUMMARY

We have formulated a process for oligomerizing olefins to distillate fuels which regenerates oligomerization catalyst beds in situ by contact with an oxygen gas at elevated temperature. The process enables continuous oligomerization for extended periods with no loss in performance.

DEFINITIONS

The term "communication" means that fluid flow is operatively permitted between enumerated components, which may be characterized as "fluid communication".

The term "downstream communication" means that at least a portion of fluid flowing to the subject in downstream communication may operatively flow from the object with which it fluidly communicates.

The term "upstream communication" means that at least a portion of the fluid flowing from the subject in upstream communication may operatively flow to the object with which it fluidly communicates.

The term "direct communication" means that fluid flow from the upstream component enters the downstream component without passing through any other intervening vessel.

The term "indirect communication" means that fluid flow from the upstream component enters the downstream component after passing through an intervening vessel.

The term "bypass" means that the object is out of downstream communication with a bypassing subject at least to the extent of bypassing.

As used herein, the term "predominant" or "predominate" means greater than 50%, suitably greater than 75% and preferably greater than 90%.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the vapor outlet of the column. The bottom temperature is the liquid bottom outlet temperature. Overhead lines and bottoms lines refer to the net lines from the column downstream of any reflux or reboil to the column. Stripper columns may omit a reboiler at a bottom of the column and instead provide heating requirements and separation impetus from a fluidized inert media such as steam. Stripping columns typically feed a top tray and take main product from the bottom.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure. As used herein, the term "boiling point temperature" means atmospheric equivalent boiling point (AEBP) as calculated from the observed boiling temperature and the distillation pressure, as calculated using the equations furnished in ASTM D1160 appendix A7 entitled "Practice for Converting Observed Vapor Temperatures to Atmospheric Equivalent Temperatures".

As used herein, the term "True Boiling Point" (TBP) means a test method for determining the boiling point of a material which corresponds to ASTM D-2892 for the production of a liquefied gas, distillate fractions, and residuum of standardized quality on which analytical data can be obtained, and the determination of yields of the above fractions by both mass and volume from which a graph of temperature versus mass % distilled is produced using fifteen theoretical plates in a column with a 5:1 reflux ratio.

As used herein, the term "T5", "T90" or "T95" means the temperature at which 5 mass percent, 90 mass percent or 95 mass percent, as the case may be, respectively, of the sample boils using ASTM D-86 or TBP.

As used herein, the term "initial boiling point" (IBP) means the temperature at which the sample begins to boil using ASTM D-7169, ASTM D-86 or TBP, as the case may be.

As used herein, the term "end point" (EP) means the temperature at which the sample has all boiled off using ASTM D-7169, ASTM D-86 or TBP, as the case may be.

As used herein, the term "diesel" means hydrocarbons boiling in the range of an IBP between about 125° C. (257° F.) and about 175° C. (347° F.) or a T5 between about 150° C. (302° F.) and about 200° C. (392° F.) and the "diesel cut point" comprising a T95 between about 343° C. (650° F.) and about 399° C. (750° F.) using the TBP distillation method or a T90 between 280° C. (536° F.) and about 340° C. (644° F.) using ASTM D-86. The term "green diesel" means diesel comprising hydrocarbons not sourced from fossil fuels.

As used herein, the term "jet fuel" means hydrocarbons boiling in the range of a T10 between about 190° C. (374° F.) and about 215° C. (419° F.) and an end point of between about 290° C. (554° F.) and about 310° C. (590° F.). The term "green jet fuel" means jet fuel comprising hydrocarbons not sourced from fossil fuels.

DETAILED DESCRIPTION

The process disclosed involves dimerizing and oligomerizing an olefin stream comprising ethylene followed by further oligomerizing ethylene oligomers. The process utilizes a zeolitic catalyst for ethylene oligomerization in a first stage and a metal catalyst for olefins oligomerization in a second stage.

Figure 1:
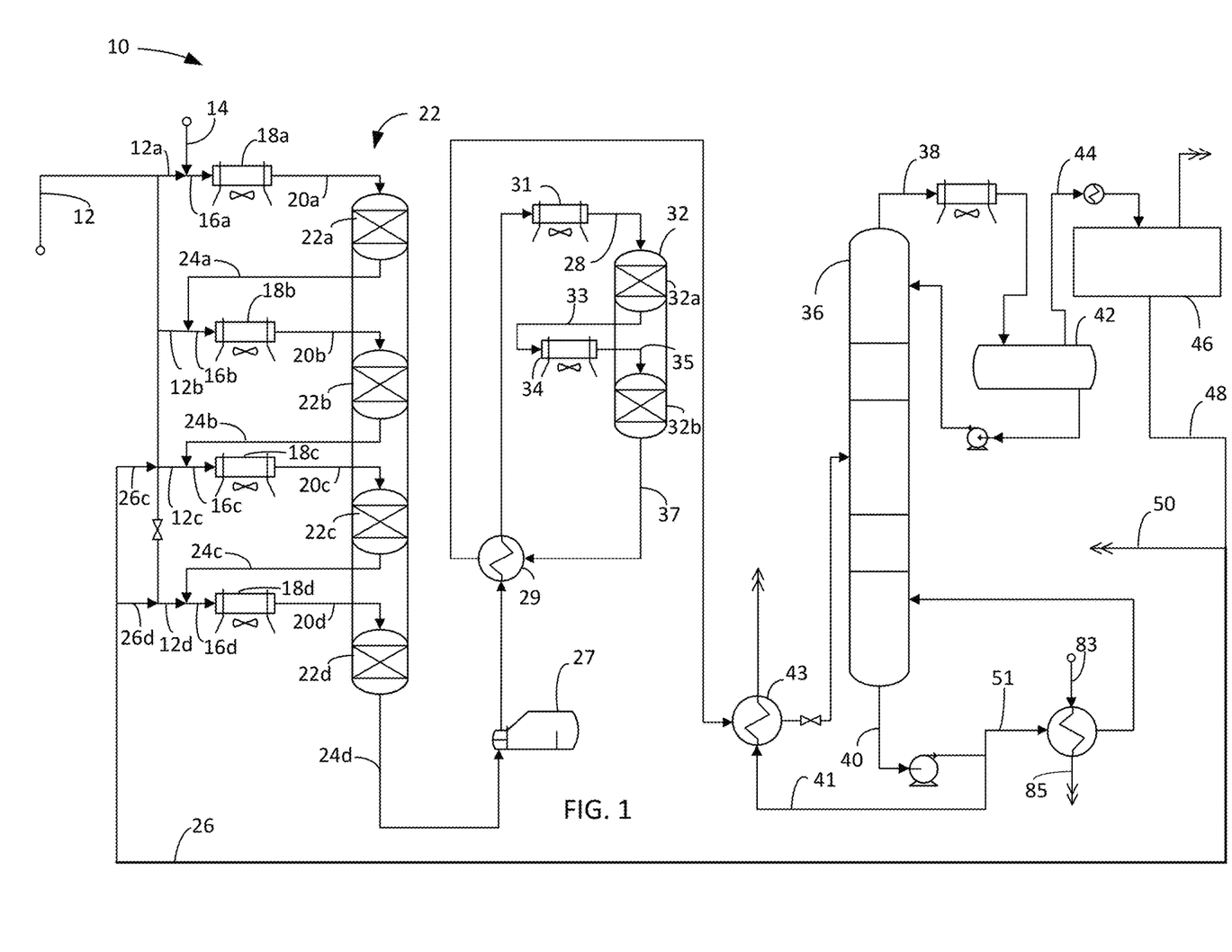
FIG. 1 is a schematic drawing of an oligomerization section of a process and apparatus of the present disclosure.
Figure 2:
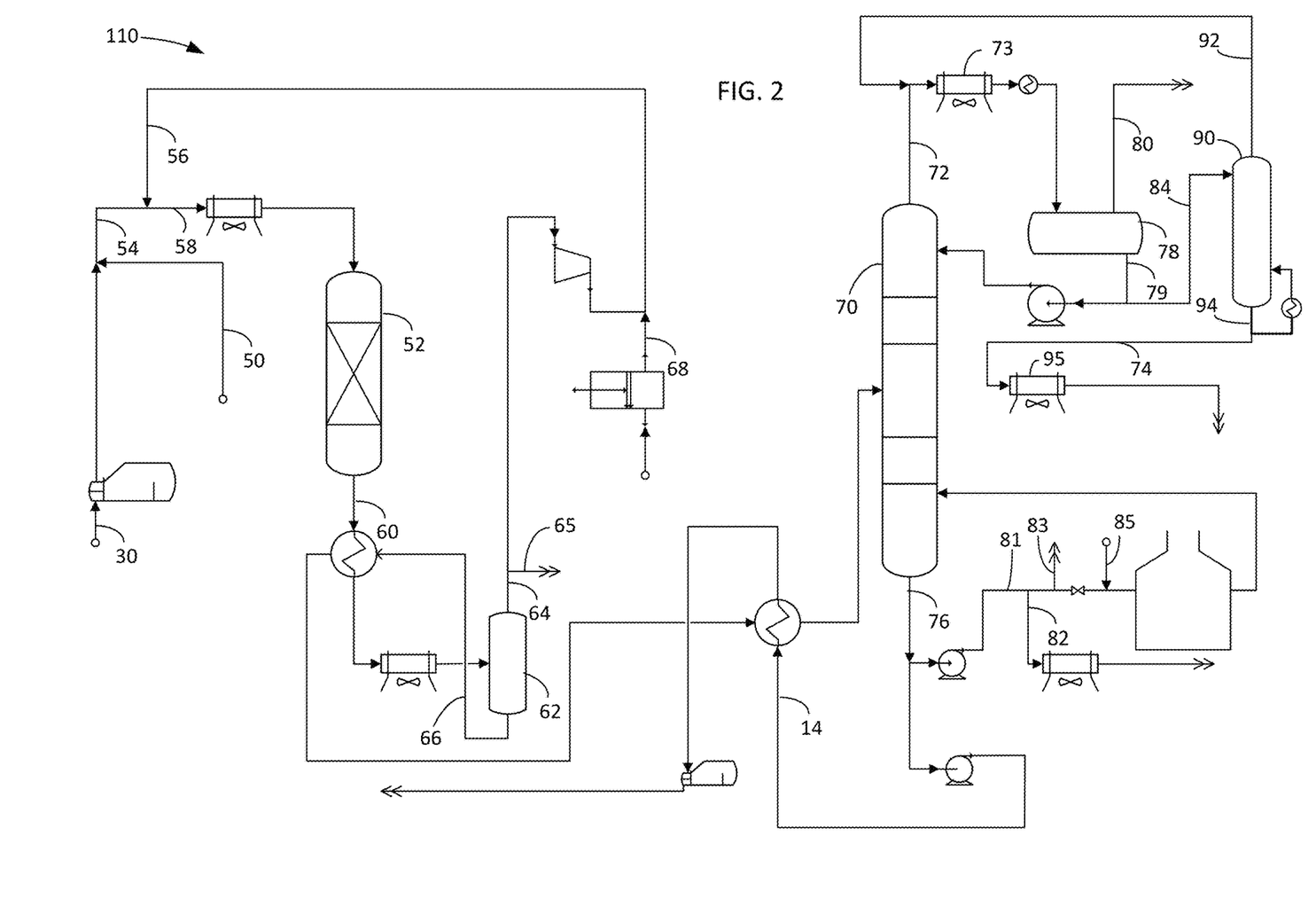
FIG. 2 is a schematic drawing of a hydrogenation section of a process and apparatus of the present disclosure.

The process and apparatus may include an oligomerization section 10 in FIG. 1 and a hydrogenation section 110 in FIG. 2.

Turning to the oligomerization section 10 of FIG. 1, a charge olefin stream in line 12 is provided to the oligomerization section 10. The charge olefin stream may comprise substantial ethylene. The charge olefin stream may predominantly comprise ethylene. In an aspect, the charge olefin stream may comprise at least 95 mol % ethylene. The charge olefin stream in line 12 may be styled an ethylene stream. The olefin stream may be provided by the dehydration of ethanol or provided from a MTO unit. The charge olefin stream may be at a temperature of about 60° C. (140° F.) to about 150° C. (302° F.), preferably about 80° C. (176° F.) to about 100° C. (212° F.) and a pressure of about 3.4 MPag (500 psig) to about 8.4 MPag (1200 psig).

The olefin stream may be initially contacted with a first-stage oligomerization catalyst to oligomerize the ethylene and/or propylene to oligomers and then contacted with a second-stage oligomerization catalyst to further oligomerize ethylene and/or propylene oligomers and unreacted ethylene and propylene. The oligomerization of ethylene generates a large exotherm. For example, dimerization of ethylene can generate 612 kcal/kg (1100 BTU/lb) of heat. Consequently, this large exotherm must be managed. Whereas dimerization of butene can generate 222 kcal/kg (400 BTU/lb) of heat.

Accordingly, the olefin stream in line 12 may be split into multiple olefin streams. In FIG. 1, the olefin stream is split into four separate streams: a first olefin stream in charge line 12a, a second olefin stream in charge line 12b, a third olefin stream in charge line 12c and a fourth or last olefin stream in charge line 12d. In an embodiment, no flow may be permitted through the control valve in charge line 12d or even through the charge line 12c, so the charge olefin stream is only fed to the upstream first stage oligomerization catalyst beds 22a-22c or just 22a-22b, respectively. More or less separate multiple olefin streams may be used. Up to six olefin streams are readily contemplated. The charge olefin stream in line 12 may be split into equal aliquot multiple olefin streams. Alternatively, the charge olefin stream in line 12 may be split into unequal streams. For example, the charge olefin stream may be split into streams of ascending flow rates in which a subsequent olefin stream has a larger flow rate than a preceding stream. In an embodiment, the charge olefin stream is split into three streams of a predominance of the flow rate of the charge olefin stream from line 12 such as about 40 to about 60% in line 12a and less than a predominance of the flow rate of the charge olefin stream from line 12 in lines 12b and 12c, such as about 15 to about 40%, and no flow in line 12d. Preferably, more of the flow rate of the charge olefin stream is fed to the upstream bed 22a of the upstream first stage oligomerization catalyst beds 22a to 22c. In an embodiment, the charge olefin stream from line 12 may be split into just lines 12a and 12b, perhaps equally. Furthermore, all of the charge olefin stream in line 12 may be directed through charge line 12a.

To manage the exotherm, the olefin stream may be diluted with a diluent stream to provide a diluted olefin stream to absorb the exotherm. The diluent stream may comprise a paraffin stream in a diluent line 14. The diluent stream in the diluent line 14 may be added to the charge olefin stream in line 12 before the charge olefin stream is split into multiple olefin streams. Preferably, the diluent stream is added to the first olefin stream in line 12a after the split into multiple olefin streams to provide a first diluted olefin stream in line 16a, so the diluent stream passes through all of oligomerization reactions. Alternatively, the diluent stream may also be split into multiple streams with each diluent stream added to a corresponding olefin stream. The diluent stream may have a volumetric flow rate of about 2 to about 8 times and preferably about 3 to about 6 times the mass flow rate of the charge olefin stream. The first diluted olefin stream may comprise no more than 17 wt % olefins, suitably no more than 10 wt % olefins and preferably no more than 6 wt % olefins. The first diluted olefin stream may comprise no more than 14 wt % ethylene, suitably no more than 10 wt % ethylene and preferably no more than 6 wt % ethylene. Similarly, the first diluted olefin stream may comprise no more than 14 wt % propylene, suitably no more than 10 wt % propylene and preferably no more than 6 wt % propylene. The first diluted olefin stream in line 16a may be cooled in a first charge cooler 18a to provide a first cooled diluted olefin stream in line 20a and charged to a first bed 22a of first stage oligomerization catalyst in a first stage oligomerization reactor 22. The cooled diluted first charge olefin stream in line 20a may be charged at a temperature of about 180° C. (356° F.) to about 260° C. (500° F.) and a pressure of about 3.5 MPag (500 psig) to about 8.4 MPag (1200 psig). The charge cooler 18a may comprise a steam generator.

The first stage oligomerization reactor 22 may comprise a series of first stage oligomerization catalyst beds 22a, 22b, 22c and 22d for charging with each multiple olefin stream 12a, 12b, 12c, and 12d, respectively. As earlier stated, in an embodiment, no charge olefin stream may be in line 12d, so the charge olefin stream from line 12 is only fed to the upstream first stage oligomerization catalyst beds 12a-12c. Alternatively, as also earlier stated, in an embodiment, no charge olefin stream may be in lines 12c or 12d, so the charge olefin stream from line 12 is only fed to the upstream first stage oligomerization catalyst beds 12a and 12b. The first stage oligomerization reactor preferably contains four fixed oligomerization catalyst beds 22a, 22b, 22c and 22d. It is also contemplated that each oligomerization catalyst bed 22a, 22b, 22c and 22d may be in a dedicated first stage oligomerization reactor or multiple first stage oligomerization catalyst beds may be in two or more separate first stage oligomerization reactors. Up to six, first stage oligomerization catalyst beds are readily contemplated. A parallel first stage oligomerization reactor may be used when the first stage oligomerization reactor 22 has deactivated during which the first stage oligomerization reactor 22 is regenerated in situ by combustion of coke from the catalyst as will be described hereinafter.

A recycle olefin stream in line 26 may be charged to the oligomerization catalyst beds 22a-22d. In an embodiment, the recycle olefin stream in line 26 is only fed to the downstream oligomerization catalyst beds 22c and 22d. The recycle olefin stream in line 26 may be split into multiple recycle olefin streams in lines 26c and 26d and only fed to oligomerization catalyst beds 22c and 22d, respectively. In an embodiment, line 26c may have a predominance of the flow rate and 26d may have the remainder of flow rate of the recycle olefin stream in line 26. Preferably, more of the flow rate of the recycle olefin stream is fed to the downstream catalyst bed 22d of the downstream catalyst beds 22c and 22d to achieve similar light olefin concentration for managing the exotherm.

The first cooled, diluted olefin stream may be charged to an upstream first, first stage oligomerization catalyst bed 22a in line 20a preferably in a down flow operation. However, upflow operation may be suitable. As oligomerization of ethylene and/or propylene occurs in the upstream first, first stage oligomerization catalyst bed 22a, an exotherm is generated due to the exothermic nature of the ethylene and/or propylene oligomerization reactions. Oligomerization of the first olefin stream produces a first oligomerized olefin stream in an upstream first oligomerized effluent line 24a at an elevated outlet temperature despite the cooling and dilution. The elevated outlet temperature is limited to between 25° C. (45° F.) and about 61° C. (110° F.) above the inlet temperature to the upstream first, first stage catalyst bed 22a.

The second olefin stream in line 12b may be diluted with the first oligomerized olefin stream in the upstream first oligomerized effluent line 24a removed from the upstream first, first stage oligomerization reactor 22 to provide a second diluted olefin stream in line 16b. The upstream first oligomerized olefin stream in line 24a includes the diluent stream from diluent line 14 added to the first olefin stream in line 12a. The second diluted olefin stream may comprise no more than 22 wt % olefins, suitably no more than 15 wt % olefins and preferably no more than 10 wt % olefins. The second diluted olefin stream may comprise no more than 15 wt % ethylene, suitably no more than 10 wt % ethylene and preferably no more than 6 wt % ethylene. The second diluted olefin stream may comprise no more than 15 wt % propylene, suitably no more than 10 wt % propylene and preferably no more than 6 wt % propylene. The second diluted olefin stream in line 16b may be cooled in a second charge cooler 18b which may be located externally to the downstream first, first stage oligomerization reactor 22 to provide a second cooled diluted olefin stream in line 20b and charged to a downstream first, first stage bed 22b of oligomerization catalyst in a first stage oligomerization reactor 22. The charge cooler 18b may comprise a steam generator. The second cooled diluted olefin stream in line 20b may be charged at a temperature of about 180° C. (356° F.) to about 260° C. (500° F.) and a pressure of about 3.4 MPag (500 psig) to about 8.4 MPag (1200 psig). The second diluted olefin stream will include diluent and olefins from the first oligomerized olefin stream. The olefins from the first oligomerized olefin stream will oligomerize in the downstream first, first stage bed catalyst bed 22b. Oligomerization of ethylene, propylene and oligomers in the second olefin stream in the downstream first, first stage bed 22b of oligomerization catalyst produces a downstream first, first stage oligomerized olefin stream in a downstream first oligomerized effluent line 24b at an elevated outlet temperature. The elevated outlet temperature may be limited to between 25° C. (45° F.) and about 61° C. (110° F.) above the inlet temperature to the catalyst bed 22b.

The third olefin stream in line 12c may be diluted with the downstream first, first stage oligomerized olefin stream in line 24b removed from the second, first stage oligomerization reactor 22b and mixed with a first recycle olefin stream in line 26c to provide a an upstream, second first stage diluted olefin stream in line 16c. The downstream first stage oligomerized olefin stream in line 24b includes the diluent stream from diluent line 14 added to the first olefin stream in line 12a. The third diluted olefin stream may comprise no more than 23 wt % olefins, suitably no more than 15 wt % olefins and preferably no more than 10 wt % olefins. The third diluted olefin stream may comprise no more than 13 wt % ethylene, suitably no more than 10 wt % ethylene and preferably no more than 6 wt % ethylene. The third diluted olefin stream may comprise no more than 13 wt % propylene, suitably no more than 10 wt % propylene and preferably no more than 6 wt % propylene. The third diluted olefin stream in line 16c may be cooled in a third charge cooler 18c which may be located externally to the first stage oligomerization reactor 22 to provide a third cooled diluted olefin stream in line 20c and charged to a third bed 22c of oligomerization catalyst in the first stage oligomerization reactor 22. The charge cooler 18c may comprise a steam generator. The third cooled diluted olefin stream in line 20c may be charged at a temperature of about 180° C. (356° F.) to about 260° C. (500° F.) and a pressure of about 3.4 MPag (500 psig) to about 8.4 MPag (1200 psig). The third diluted olefin stream will include diluent and olefins from the downstream second, first stage oligomerized olefin stream and from the first recycle olefin stream. The olefins from the downstream first, first stage oligomerized olefin stream and the first recycle olefin stream will oligomerize in the upstream second, first stage catalyst bed 22c. Oligomerization of ethylene and propylene in the third diluted olefin stream in the upstream second, first stage bed 22c of oligomerization catalyst produces an upstream second, first stage oligomerized olefin stream in a upstream second, first stage oligomerized effluent line 24c at an elevated outlet temperature. In an embodiment, the upstream second, first stage oligomerized olefin stream is a penultimate oligomerized olefin stream and the upstream second, first stage oligomerized effluent line 24c is a penultimate oligomerized effluent line 24c. The elevated outlet temperature is limited to between 25° C. (45° F.) and about 61° C. (110° F.) above the inlet temperature to the catalyst bed 22c.

The fourth olefin stream in line 12d may be diluted with the upstream second, first stage or penultimate oligomerized olefin stream in line 24c removed from the upstream second, first stage oligomerization reactor 22 and the second recycle olefin stream in line 26d to provide a fourth diluted olefin stream in line 16d. The upstream second, first stage or penultimate oligomerized olefin stream in line 24c includes the diluent stream from diluent line 14 added to the first olefin stream in line 12a. The fourth diluted olefin stream may comprise no more than 24 wt % olefins, suitably no more than 18 wt % olefins and preferably no more than 10 wt % olefins. The fourth diluted olefin stream may comprise no more than 11 wt % ethylene, suitably no more than 8 wt % ethylene and preferably no more than 6 wt % ethylene. The fourth diluted olefin stream may comprise no more than 11 wt % propylene, suitably no more than 8 wt % propylene and preferably no more than 6 wt % propylene. The fourth diluted olefin stream in line 16d may be cooled in a fourth charge cooler 18d which may be located externally to the first stage oligomerization reactor 22 to provide a fourth cooled diluted olefin stream in line 20d and charged to a downstream second, first stage bed 22d of oligomerization catalyst in the first stage oligomerization reactor 22. The charge cooler 18d may comprise a steam generator. The fourth cooled diluted olefin stream in line 20d may be charged at a temperature of about 180° C. (356° F.) to about 260° C. (500° F.) and a pressure of about 3.4 MPag (500 psig) to about 8.4 MPag (1200 psig). The fourth or last diluted olefin stream will include diluent and olefins from the upstream, second, first stage or penultimate oligomerized olefin stream and the second recycle olefin stream. The olefins from the upstream, second, first stage or penultimate oligomerized olefin stream and the second recycle olefin stream will oligomerize in the downstream, second, first stage catalyst bed 22d. Oligomerization of ethylene and propylene in the fourth olefin stream in the downstream second, first stage bed 22d of oligomerization catalyst produces a downstream, second first stage oligomerized olefin stream in a fourth oligomerized effluent line 24d at an elevated outlet temperature. The elevated outlet temperature is limited to between 25° C. (45° F.) and about 61° C. (110° F.) above the inlet temperature to the downstream second, first stage catalyst bed 22d.

The recycle olefin stream 26c and 26d provide olefins that can oligomerize over the catalyst beds 22c and 22d, respectively, but can also help manage the exotherm generated during oligomerization of ethylene.

In an embodiment, the downstream second, first stage oligomerized olefin stream is a last olefin stream, and the downstream second, first stage oligomerized effluent line 24d is a last oligomerized effluent line 24d.

The oligomerization reaction takes place predominantly in the liquid phase or in a mixed liquid and gas phase at a LHSV 0.5 to 10 hr$^{-1}$ on an olefin basis. We have found that a predominant fraction of ethylene in the olefin stream converts to higher olefins. Typically, at least 20 to about 40 mol % of ethylene will oligomerize across an oligomerization catalyst bed. The ethylene will initially oligomerize over the catalyst to butenes.

The first stage oligomerization catalyst may include a zeolitic catalyst. The first stage oligomerization catalyst may be considered a solid acid catalyst. The zeolite may comprise between about 5 and about 95 wt % of the catalyst, for example between about 5 and about 85 wt %. Suitable zeolites include zeolites having a structure from one of the following classes: MFI, MEL, ITH, IMF, TUN, FER, BEA, FAU, BPH, MEI, MSE, MWW, UZM-8, MOR, OFF, MTW, TON, MTT, AFO, ATO, and AEL. 3-letter codes indicating a zeotype are as defined by the Structure Commission of the International Zeolite Association and are maintained at http://www.iza-structure.org/databases. UZM-8 is as described in U.S. Pat. No. 6,756,030. In a preferred aspect, the first stage oligomerization catalyst may comprise a zeolite with a framework having a ten-ring pore structure. Examples of suitable zeolites having a ten-ring pore structure include TON, MTT, MFI, MEL, AFO, AEL, EUO and FER. In a further preferred aspect, the first stage oligomerization catalyst comprising a zeolite having a ten-ring pore structure may comprise a uni-dimensional pore structure. A uni-dimensional pore structure indicates zeolites containing non-intersecting pores that are substantially parallel to one of the axes of the crystal. The pores preferably extend through the zeolite crystal. Suitable examples of zeolites having a ten-ring uni-dimensional pore structure may include MTT. In a further aspect, the first stage oligomerization catalyst comprises an MTT zeolite.

The first stage oligomerization catalyst may be formed by combining the zeolite with a binder, and then forming the catalyst into pellets. The pellets may optionally be treated with a phosphorus reagent to create a zeolite having a phosphorous component between 0.5 and 15 wt % of the treated catalyst. The binder is used to confer hardness and strength on the catalyst. Binders include alumina, aluminum phosphate, silica, silica-alumina, zirconia, titania and combinations of these metal oxides, and other refractory oxides, and clays such as montmorillonite, kaolin, palygorskite, smectite and attapulgite. A preferred binder is an aluminum-based binder, such as alumina, aluminum phosphate, silica-alumina and clays.

One of the components of the catalyst binder utilized in the present disclosure is alumina. The alumina source may be any of the various hydrous aluminum oxides or alumina gels such as alpha-alumina monohydrate of the boehmite or pseudo-boehmite structure, alpha-alumina trihydrate of the gibbsite structure, beta-alumina trihydrate of the bayerite structure, and the like. A suitable alumina is available from UOP LLC under the trademark VERSAL. A preferred alumina is available from Sasol North America Alumina Product Group under the trademark Catapal. This material is an extremely high purity alpha-alumina monohydrate (pseudo-boehmite) which after calcination at a high temperature has been shown to yield a high purity gamma-alumina.

A suitable first stage oligomerization catalyst is prepared by mixing proportionate volumes of zeolite and alumina to achieve the desired zeolite-to-alumina ratio. In an embodiment, the MTT content may about 5 to about 85, for example about 20 to about 82 wt % MTT zeolite, and the balance alumina powder will provide a suitably supported catalyst. A silica support is also contemplated.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried. Extrusion aids such as cellulose ether powders can also be added. A preferred extrusion aid is available from The Dow Chemical Company under the trademark Methocel.

The paste or dough may be prepared in the form of shaped particulates, with the preferred method being to extrude the dough through a die having openings therein of desired size and shape, after which the extruded matter is broken into extrudates of desired length and dried. A further step of calcination may be employed to give added strength to the extrudate. Generally, calcination is conducted in a stream of air at a temperature from about 260° C. (500° F.) to about 815° C. (1500° F.). The MTT catalyst is not selectivated to neutralize acid sites such as with an amine.

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as m; however, it is usually about 0.635 mm (0.25 inch) to about 12.7 mm (0.5 inch), preferably about 0.79 mm (1/32 inch) to about 6.35 mm (0.25 inch), and most preferably about 0.06 mm (1/24 inch) to about 4.23 mm (1/6 inch).

In one exemplary embodiment, an MTT-type zeolite catalyst disposed on a high purity pseudo boehmite alumina substrate in a ratio of about 90/10 to about 20/80 and preferably between about 20/80 and about 50/50 is provided in a catalyst bed or more in the first stage oligomerization reactor 22.

The first stage oligomerization catalyst can be regenerated upon deactivation. Suitable regeneration conditions include subjecting the first stage oligomerization catalyst, for example, in situ, to hot air at 500° C. for 3 hours. In practice, regeneration may be effected by hot nitrogen purge at about 300 to about 500° C., suitably about 350 to about 450° C. to strip heavy hydrocarbon species from the spent catalyst. Alternatively, the spent catalyst may be purged with a stream of light olefins, may be washed with a solvent, or with another hydrocarbon stream. The purge or wash step is followed by coke burn in about 0.3 to about 0.7 mol % oxygen for 20 to 40 hours and a proof burn in about 3 to about 10 mol % oxygen until all coke is burned, or at least no more than 1.2 wt % coke on catalyst. To facilitate regeneration without downtime, a swing bed arrangement may be employed with an alternative first stage oligomerization reactor. Alternatively, a lead-lag swing bed arrangement may be employed. A regeneration gas stream may be admitted to the first stage oligomerization reactor 22 requiring regeneration. The regeneration gas may comprise air with an increased or decreased concentration of oxygen. Activity and selectivity of the regenerated catalyst is comparable to fresh catalyst.

The zeolite catalyst is advantageous as a first stage oligomerization catalyst. The zeolitic catalyst has relatively low sensitivity towards oxygenates contamination. Consequently, less removal of oxygenates is required of olefinic feed in line 12 if produced from an ethanol dehydration process.

The last oligomerized olefin stream in the last oligomerized effluent line 24d has an increased concentration of ethylene dimers and oligomers compared to the charge olefin stream in line 12. The oligomerized olefin stream is cooled to generate steam in a steam generator 27, then cooled by heat exchange with an oligomerized stream in line 37 in a heat exchanger 29 and then cooled in an air cooler 31 before it is charged to a second stage oligomerization reactor 32 in an oligomerization charge line 28. The second stage oligomerization reactor 32 may comprise a series of second stage oligomerization catalyst beds 32a and 32b in series. It is also contemplated that each second stage oligomerization catalyst bed 32a and 32b may be in a dedicated second stage oligomerization reactor or multiple second stage oligomerization catalyst beds may be in two or more separate second stage oligomerization reactors. More than two second stage oligomerization catalyst beds are readily contemplated. A parallel second stage oligomerization reactor may be used when the second stage oligomerization reactor 32 has deactivated during which the second stage oligomerization reactor 32 is regenerated in situ by combustion of coke from the catalyst.

To achieve the most desirable olefin product, the second stage oligomerization reactor 32 is operated at a temperature from about 38° C. (100° F.) to about 180° C. (356° F.). The second stage oligomerization reactor 32 is run at a pressure of about 4.9 MPa (700 psig) to about 7.6 MPa (1100 psig), and more preferably from about 3.4 MPa (500 psig) to about 6.9 MPa (1000 psig). A first oligomerate stream from the first second stage oligomerization catalyst bed 32a may be withdrawn from the first, second stage oligomerization reactor 32 in line 33, cooled in a cooler 34 back to a temperature of about 38° C. (100° F.) to about 180° C. (356° F.) and charged to the second, second stage oligomerization catalyst bed 32b in line 35.

The second stage oligomerization reactor 32 may be in downstream communication with the first stage oligomerization reactor 22. The second stage oligomerization reactor 32 preferably operates in a down flow operation. However, upflow operation may be suitable. The charge oligomerized olefin stream is contacted with the second stage oligomerization catalyst causing the C2-C8 olefins to dimerize and trimerize to provide distillate range olefins. With regard to the second stage oligomerization reactor 32, process conditions are selected to produce a higher percentage of jet range olefins which, when hydrogenated in a subsequent step as will be described below, result in a desirable jet-range hydrocarbon product. A predominance of the unconverted ethylene in the charge oligomerized olefin stream is oligomerized in the second stage oligomerization reactor 32. In an embodiment, at least 90 mol % of ethylene in the charge oligomerized olefin stream is oligomerized in the second stage oligomerization reactor 32. The metal, second stage oligomerization catalyst is efficient at dimerizing un-dimerized ethylene. An oligomerate olefin stream with an increased average carbon number greater than the oligomerized olefin stream charged in the oligomerization charge line 28 exits the oligomerization reactor 32 in line 37.

The second stage oligomerization catalyst is preferably an amorphous silica-alumina base with a metal from either Group VIII and/or Group VIB in the periodic table using Chemical Abstracts Service notations. In an aspect, the catalyst has a Group VIII metal promoted with a Group VIB metal. Typically, the silica and alumina will only be in the base, so the silica-to-alumina ratio will be the same for the catalyst as for the base. The metals can either be impregnated onto or ion exchanged with the silica-alumina base. Co-mulling is also contemplated. Catalysts for the present invention may have a Low Temperature Acidity Ratio of at least about 0.15, suitably of about 0.2, and preferably greater than about 0.25, as determined by Ammonia Temperature Programmed Desorption (Ammonia TPD) as described hereinafter. Additionally, a suitable second stage oligomerization catalyst will have a surface area of between about 50 and about 400 m$^2$/g as determined by nitrogen BET.

The preferred second stage oligomerization catalyst comprises an amorphous silica-alumina support. One of the components of the catalyst support utilized in the present invention is alumina. The alumina may be any of the various hydrous aluminum oxides or alumina gels such as alpha-alumina monohydrate of the boehmite or pseudo-boehmite structure, alpha-alumina trihydrate of the gibbsite structure, beta-alumina trihydrate of the bayerite structure, and the like. A particularly preferred alumina is available from Sasol North America Alumina Product Group under the trademark Catapal. This material is an extremely high purity alpha-alumina monohydrate (pseudo-boehmite) which after calcination at a high temperature has been shown to yield a high purity gamma-alumina. Another component of the catalyst support is an amorphous silica-alumina. A suitable silica-alumina with a silica-to-alumina ratio of 2.6 is available from CCIC, a subsidiary of JGC, Japan.

Another component utilized in the preparation of the second stage oligomerization catalyst utilized in the present invention is a surfactant. The surfactant is preferably admixed with the hereinabove described alumina and the silica-alumina powders. The resulting admixture of surfactant, alumina and silica-alumina is then formed, dried and calcined as hereinafter described. The calcination effectively removes by combustion the organic components of the surfactant but only after the surfactant has dutifully performed its function in accordance with the present invention. Any suitable surfactant may be utilized. A preferred surfactant is a surfactant selected from a series of commercial surfactants sold under the trademark "Antarox" by Solvay S. A. The "Antarox" surfactants are generally characterized as modified linear aliphatic polyethers and are low-foaming biodegradable detergents and wetting agents.

A suitable silica-alumina mixture is prepared by mixing proportionate volumes silica-alumina and alumina to achieve the desired silica-to-alumina ratio. In an embodiment, about 75 to about 95 wt-% amorphous silica-alumina with a silica-to-alumina ratio of 2.6 and about 10 to about 20 wt-% alumina powder will provide a suitable support. In an embodiment, other ratios of amorphous silica-alumina to alumina may be suitable.

Any convenient method may be used to incorporate a surfactant with the silica-alumina and alumina mixture. The surfactant is preferably admixed during the admixture and formation of the alumina and silica-alumina. A preferred method is to admix an aqueous solution of the surfactant with the blend of alumina and silica-alumina before the final formation of the support. It is preferred that the surfactant be present in the paste or dough in an amount from about 0.01 to about 10 wt-% based on the weight of the alumina and silica-alumina.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried.

The paste or dough may be prepared in the form of shaped particulates, with the preferred method being to extrude the dough mixture of alumina, silica-alumina, surfactant and water through a die having openings therein of desired size and shape, after which the extruded matter is broken into extrudates of desired length and dried. A further step of calcination may be employed to give added strength to the extrudate. Generally, calcination is conducted in a stream of dry air at a temperature from about 260° C. (500° F.) to about 815° C. (1500° F.).

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as m; however, it is usually about 0.635 mm (0.25 inch) to about 12.7 mm (0.5 inch), preferably about 0.79 mm (1/32 inch) to about 6.35 mm (0.25 inch), and most preferably about 0.06 mm (1/24 inch) to about 4.23 mm (1/6 inch).

Typical characteristics of the amorphous silica-alumina supports utilized herein are a total pore volume, average pore diameter and surface area large enough to provide substantial space and area to deposit the active metal components. The total pore volume of the support, as measured by conventional mercury porosimeter methods, is usually about 0.2 to about 2.0 cc/gram, preferably about 0.25 to about 1.0 cc/gram and most preferably about 0.3 to about 0.9 cc/gram. Ordinarily, the amount of pore volume of the support in pores of diameter greater than 100 angstroms is less than about 0.1 cc/gram, preferably less than 0.08 cc/gram, and most preferably less than about 0.05 cc/gram. Surface area, as measured by the B.E.T. method, is typically above 50 m$^2$/gram, e.g., above about 200 m$^2$/gram, preferably at least 250 m$^2$/gram., and most preferably about 300 m$^2$ gram to about 400 m$^2$/gram.

To prepare the catalyst, the support material is compounded, as by a single impregnation or multiple impregnations of a calcined amorphous refractory oxide support particles, with one or more precursors of at least one metal component from Group VIII or VIB of the periodic table. The Group VIII metal, preferably nickel, should be present in a concentration of about 0.5 to about 15 wt-% and the Group VIB metal, preferably tungsten, should be present in a concentration of about 0 to about 12 wt-%. The impregnation may be accomplished by any method known in the art, as for example, by spray impregnation wherein a solution containing the metal precursors in dissolved form is sprayed onto the support particles. Another method is the multi-dip procedure wherein the support material is repeatedly contacted with the impregnating solution with or without intermittent drying. Yet other methods involve soaking the support in a large volume of the impregnation solution or circulating the support therein, and yet one more method is the pore volume or pore saturation technique wherein support particles are introduced into an impregnation solution of volume just sufficient to fill the pores of the support. On occasion, the pore saturation technique may be modified, so as to utilize an impregnation solution having a volume between 10 percent less and 10 percent more than that which will just fill the pores.

If the active metal precursors are incorporated by impregnation, a subsequent or second calcination at elevated temperatures, as for example, between 399° C. (750° F.) and 760° C. (1400° F.), converts the metals to their respective oxide forms. In some cases, calcinations may follow each impregnation of individual active metals. A subsequent calcination yields a catalyst containing the active metals in their respective oxide forms.

A preferred second stage oligomerization catalyst of the present invention has an amorphous silica-alumina base impregnated with 0.5-15 wt-% nickel in the form of 3.175 mm (0.125 inch) extrudates and a density of about 0.45 to about 0.65 g/ml. It is also contemplated that metals can be incorporated onto the support by other methods such as ion-exchange and co-mulling.

The second stage oligomerization catalyst can be regenerated upon deactivation. Suitable regeneration conditions include subjecting the catalyst, for example, in situ, to hot air at 500° C. for 3 hours. In practice, regeneration may be effected by hot nitrogen purge at about 300 to about 500° C., suitably about 350 to about 450° C. to strip heavy hydrocarbon species from the spent catalyst. Alternatively, the spent catalyst may be purged with a stream of light olefins, may be washed with a solvent, or with another hydrocarbon stream. The purge or wash step is followed by coke burn in about 0.3 to about 0.7 mol % oxygen for 20 to 40 hours and a proof burn in about 3 to about 10 mol % oxygen until all coke is burned. To facilitate regeneration without downtime, a swing bed arrangement may be employed with an alternative second stage oligomerization reactor. The regeneration gas may comprise air with an increased or decreased concentration of oxygen. Activity and selectivity of the regenerated catalyst is comparable to fresh catalyst.

Second stage oligomerization reactions are also exothermic in nature. The last oligomerized olefin stream in line 24*d* includes the diluent stream from diluent line 14 added to the first olefin stream in line 12*a* and carried through the first stage oligomerization catalyst beds 22*a*-22*d*. The diluent stream is then transported into the second stage oligomerization reactor 32 in line 28 to absorb the exotherm in the second stage oligomerization reactor. It is contemplated to introduce diluent to the second stage oligomerization catalyst beds 22a-22d with or without it first passing through the first stage oligomerization catalyst beds.

When the oligomerization reaction is performed according to the above-noted process conditions, a C4 olefin conversion of greater than or equal to about 95% is achieved, or greater than or equal to 97%. The resulting oligomerate olefin stream in line 37 includes a plurality of olefin products that are distillate range hydrocarbons.

An oligomerate olefin stream in line 37 with an increased C9+ olefin concentration compared to the oligomerized olefin stream in line 28 heat exchanged with the last oligomerized olefin stream in line 24d in the heat exchanger 29 and an olefin splitter bottoms stream in line 41 in a heat exchanger 43, let down in pressure and fed to olefin splitter column 36. The oligomerized olefin stream in line 37 is at a temperature from about 140° C. (284° F.) to about 200° C. (392° F.) and a pressure of about 3.9 MPa (gauge) (550 psig) to about 6.3 MPa (gauge) (900 psig).

In the olefin splitter column 36 oligomers that boil lower than the jet range hydrocarbons, typically C8- hydrocarbons with atmospheric boiling points less than about 150° C., are separated in an olefin splitter overhead stream in an overhead line 38 from a bottoms stream in a bottoms line 40 comprising distillate-range C9+ hydrocarbons, typically C9-C22 olefins. The olefin splitter column 36 may be operated at a bottoms temperature of about 200° C. (400° F.) to about 315° C. (600° F.) and an overhead pressure of about 35 kPa (gauge) (5 psig) to about 350 kPa (gauge) (50 psig). It is envisioned that the olefin splitter column 36 may be two columns.

The olefin splitter overhead stream may be cooled to about 66° C. (150° F.) to about 93° C. (200° F.) and a resulting condensate portion refluxed from an olefin splitter receiver 42 back to the olefin splitter column 36. A net vapor stream in a receiver overhead line 44 from the olefin splitter receiver 42 may be compressed up to oligomerization pressure in an off-gas compressor 46 to provide a light oligomer stream in line 48 either in vapor phase or in liquid phase after cooling. Alternatively, the olefin splitter overhead stream in the receiver overhead line 44 may be fully condensed by cooling perhaps in an external refrigeration loop to provide a liquid light oligomer stream in line 48. Line 48 may also be taken from receiver 42. The light oligomer stream in line 48 may be split between a light olefin drag stream in line 50 and the oligomer recycle stream in line 26 that may be recycled to the second stage oligomerization reactor 32 or to the first stage oligomerization reactor 22. The light olefin drag stream in line 50 may comprise about 1 to about 15 wt % of the light oligomer stream in line 48. The light oligomer stream in line 48 may comprise about 30 to about 80 wt % light olefins.

In an embodiment, the oligomer recycle stream in line 26 may be mixed with the last oligomerized olefin stream in the last dimerized effluent line 24d to provide the charge oligomerization stream in line 28 for charge to the second stage oligomerization reactor 32. The oligomer recycle stream in line 26 may be mixed with the first diluted olefin stream in line 16a or more suitably divided up between the first through fourth diluted olefin streams in lines 16a-16d to oligomerize unreacted C4-C7 olefins. In a preferred embodiment, the oligomer recycle stream in line 26 may be split into a first oligomer recycle stream in line 26c and a second oligomer recycle stream in line 26d. The first oligomer recycle stream in line 26c may be mixed with the upstream second, first stage oligomerized olefin stream in the downstream first, first stage oligomerized effluent line 24b and perhaps the third olefin stream in the third olefin line 12c to provide the third diluted olefin stream in line 16c for charge to the upstream second, first-stage oligomerization catalyst bed 22c. The second oligomer recycle stream in line 26d may be mixed with the upstream second, first stage oligomerized olefin stream in the upstream second, first stage oligomerized effluent line 24c and perhaps the third olefin stream in the third olefin line 12c to provide the fourth diluted olefin stream in line 16d for charge to the downstream second, first-stage oligomerization catalyst bed 22d.

The heavy olefin stream in the splitter bottoms line 40 may be split between a reboil stream in line 51 that is reboiled and fed back to the olefin splitter column 36 and a heavy olefin stream in a net splitter bottoms line 41. The heavy olefin stream in the net bottoms line 30 is cooled by heat exchange with the oligomerized olefin stream in line 37 and then transported to the hydrogenation section 110 in FIG. 2. The reboil stream in line 51 may be heated by heat exchange with a reboil stream in line 83 from the jet fractionation bottoms line 76 which is returned to the jet fractionation column in line 85 in FIG. 2.

Turning to the hydrogenation section 110 in FIG. 2, the heavy olefin stream in the net olefin splitter bottoms line 30 from FIG. 1 comprising distillate-range C9+ oligomerized olefins may be hydrogenated to saturate the olefinic bonds in a hydrogenation reactor 52 to provide fuels. This step is performed to ensure the product motor fuel meets or exceeds the thermal oxidation requirements specified in ASTM D7566-10a for hydroprocessed synthesized paraffinic kerosene (SPK). Additionally, saturating the oligomerized heavy olefins will provide the paraffin stream that may be used as the diluent stream in line 14. The heavy olefin stream in line 30 may be cooled to produce steam and be combined with the light olefin drag stream comprising C2 to C8 olefins in line 50 also from FIG. 1 to produce a combined olefin stream in line 54. The combined olefin stream in line 54 may also be combined with a hydrogen stream in line 56 to provide a combined hydrogenation charge stream in line 58 which is cooled and charged to the hydrogenation reactor 52 at 125° C. (257° F.) to about 315° C. (600° F.) and 3.5 MPag (500 psig) to about 6.9 MPag (1000 psig). An excess of hydrogen may be employed to ensure complete saturation such as about 1.5 to about 2.5 of stochiometric hydrogen.

Hydrogenation is typically performed using a conventional hydrogenation or hydrotreating catalyst, and can include metallic catalysts containing, e.g., palladium, rhodium, nickel, ruthenium, platinum, rhenium, cobalt, molybdenum, or combinations thereof, and the supported versions thereof. Catalyst supports can be any solid, inert substance including, but not limited to, oxides such as silica, alumina, titania, calcium carbonate, barium sulfate, and carbons. The catalyst support can be in the form of powder, granules, pellets, or the like.

In an exemplary embodiment, hydrogenation is performed in the hydrogenation reactor 52 that includes a platinum-on-alumina catalyst, for example about 0.5 wt % to about 0.9 wt % platinum-on-alumina catalyst. The hydrogenation reactor 52 converts the olefins into a paraffin product having the same carbon number distribution as the olefins, thereby forming distillate-range paraffins suitable for use as jet and diesel fuel.

The saturated heavy stream discharged from the hydrogenation reactor 52 in line 60 may be cooled by heat exchange with a saturated heavy liquid stream in a separator bottoms line 66 and fed to a hydrogenation separator 62. In the hydrogenation separator 62, the saturated heavy stream is separated into a hydrogenated separator vapor stream in an overhead line 64 and the saturated heavy liquid stream in the hydrogenation separator bottoms line 66. A purge in line 65 may be taken from the hydrogenated separator vapor stream in line 64 and the remainder may be compressed and combined with make-up hydrogen in line 68 to provide the hydrogen stream in line 56. The saturated heavy liquid stream in the bottoms line 66 may be heated by heat exchange with the saturated heavy stream in line 60 and the diluent stream in line 14 and fed to a jet fractionation column 70. In an embodiment, a hot separator and cold separator system may be substituted for a single hydrogenation separator 62.

The saturated heavy liquid stream in the bottoms line 66 may be fed to the jet fractionation column 70 without undergoing prior stripping in a stripper column. Alternatively, a stripper column may be utilized upstream of the jet fractionation column 70. In the jet fractionation column 70, the saturated heavy liquid stream may be separated into a net off-gas stream in a net overhead line 80, a green jet stream in a net liquid overhead line 74 and a green diesel stream in a net bottoms line 82. The jet fractionation column 70 may be operated at a bottoms temperature of about 316° C. (600° F.) to about 482° C. (900° F.) and an overhead pressure of about 35 kPa (5 psig) to about 350 kPa (50 psig).

A jet fractionation overhead stream in the overhead line 72 may be cooled and a resulting condensate stream is produced in line 79 from a bottom of the receiver 78. A portion of the condensate in line 79 is refluxed back to the jet fractionation column 70 while a jet fuel stream in line 84 is transported to a jet stripper column 90. The net off gas stream comprising C8– hydrocarbons is taken in a receiver overhead line 80 from the jet fractionation receiver 78. Most of the hydrocarbons in the net off gas stream in the receiver overhead line 80 are lighter hydrocarbons and can be used to fuel the reboiler for the jet fractionation column 70, the olefin splitter column 36 and/or other fired heater in the complex.

The jet stripper column 90 strips light ends from the jet fuel stream in line 84 and sends them in the overhead line 92 back to the condenser 73 with the jet fractionation overhead stream in line 72. A stripped jet fuel product is taken in the jet stripper bottoms line 94 while a portion is reboiled and fed back to the jet stripper column 90. A jet fuel product stream in line 74 is taken from the stripped jet fuel product in line 94, cooled in the cooler 95 and recovered as jet fuel product. The green jet stream taken in the line 74 comprises kerosene range C9-C17 hydrocarbons and may be cooled and taken as product meeting applicable SPK standards. In an alternative embodiment, the green jet stream may be taken from a side line from the side of the jet fractionation column 70.

The green diesel bottoms stream in the bottoms line 76 may be split between a reboil stream in line 81 that is reboiled and fed back to the jet fractionation column 70, a green diesel product stream in line 82 and a diluent stream in line 14. The diluent stream in line 14 may be cooled by heat exchange with the separator bottoms line 66 and by steam generation and recycled back to be mixed with the olefin stream in line 12 in the oligomerization section 10 in FIG. 1, preferably the first olefin stream in line 12a, to provide the first diluted olefin stream in line 16a to absorb the exotherm in the first stage oligomerization reactor 22. The green diesel in the diluent line 14 is paraffinic, so it will be inert to the oligomerization and hydrogenation reactions to which it may be subject. Both the jet fuel stream in the line 74 and the diesel stream in line 82 can be cooled and fed to their respective fuel pools. The diesel stream will meet ASTM D975 standards for diesel. The reboil stream in line 81 may be diverted in line 83 to the olefin splitter column 70 to reboil the reboil stream in line 51 from the olefin splitter bottoms stream in line 40 in FIG. 1. The cooled reboil stream may be returned in line 85 and heated in the heater to boiling and returned to the jet fractionation column 70.

Starting with ethylene, the disclosed process can efficiently produce green jet fuel and green diesel fuel that meets applicable fuel requirements while managing exothermic heat generation. Carbon recovery in the process can exceed 95%.

At the end of the 15 or 20 days, suitably after the end of two weeks or more preferably at least after 30 days, after the maximum temperature is reached to compensate for declining catalytic activity, the catalytic cycle in both the first stage oligomerization reactor 22 and/or the second stage oligomerization reactor 32 must restart. The catalysts have to be regenerated to recover their initial activity. The regeneration of the zeolitic oligomerization catalyst in the first stage oligomerization reactor 22 is conducted by taking the first stage oligomerization reactor 22 offline by discontinuing olefin charge thereto. The reactor is depressurized to about 280 kPa (g) (40 psig) to about 600 kPa (g) (85 psig) and drained of liquid perhaps by pumping it to the olefin splitter column 36. The first stage oligomerization reactor 22 is then purged with hot, dry purge gas to strip heavy hydrocarbons, C8 to C21, from the first stage oligomerization catalyst. An inert gas such as nitrogen, a hydrocarbon stream or a solvent may be used as a purge gas. The purge gas may be introduced to the first stage oligomerization reactor 22 in down flow and at about 350 to about 450° C. and about 175 kPa (g) (25 psig) to about 280 kPa (g) (40 psig), sufficiently high to recover light olefins in the liquid phase. Once liquid olefins are fully recovered, the flow of purge gas to the first stage oligomerization reactor 22 is terminated. Air supply is then routed to the first stage oligomerization reactor for about 10 to about 25 hours. At the inlet, oxygen concentration should not exceed about 0.3 to about 0.7 mol % and at the outlet, the temperature be no more than 400° C. to about 500° C. Once the exotherm from the burn no longer rises, the oxygen concentration can be increased to about 5 mol % to about 10 mol % to prove that carbon is sufficiently combusted. GHSV based on the total flow rate ranges from about 400 to about 4000 $hr^{-1}$ and preferably no more than 1000 $hr^{-1}$. The oxygen can then be purged from the first stage oligomerization reactor by an inert gas purge or by filling it with a paraffinic liquid. The regeneration of the second stage oligomerization catalyst in the second stage oligomerization reactor 32 comprising metal on a support may be conducted according to the same procedure.

Figure 3:
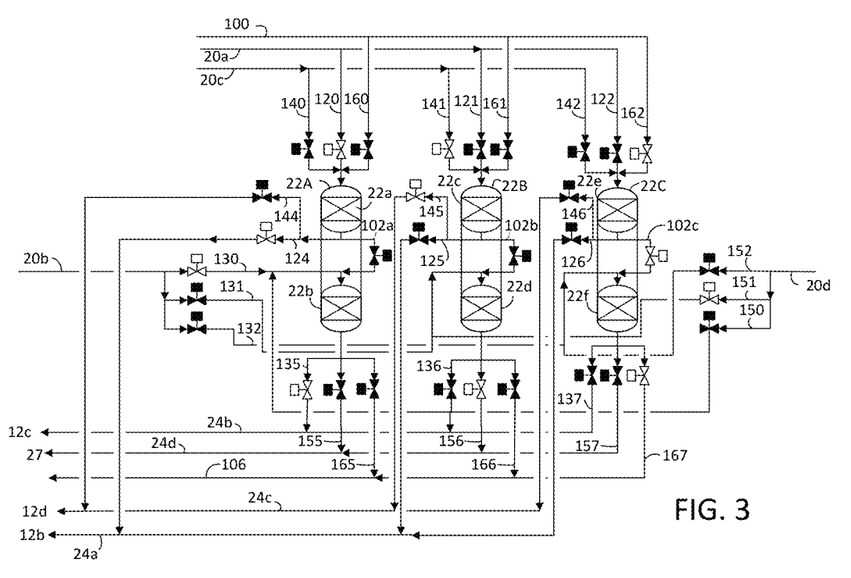
FIG. 3 is a schematic drawing of a regeneration process for the oligomerization section of a process and apparatus of the present disclosure.

We have developed a process for regenerating both catalyst systems in the first stage oligomerization reactor 22 and the second stage oligomerization reactor 32 which allows continuous operation. FIG. 3 illustrates a process for regeneration of the first stage oligomerization reactors 22.

The process may utilize three first stage oligomerization reactors 22, a first reactor 22A, a second reactor 22B and a third reactor 22C. The three reactors switch between lead, lag and regeneration mode. In FIG. 3, the first reactor 22A is in lead mode, the second reactor 22B is in lag mode and the third reactor 22C is in regeneration mode. FIG. 3 relates to FIG. 1. In FIG. 3, unfilled valves are open and filled valves are closed. Furthermore, capital letters in the reference characters are distinct from lower case letters.

Line 20a of FIG. 1 charges the first cooled diluted olefin stream through an open valve on a connecting line 120 to the upstream first, first stage oligomerization catalyst bed 22a of the first reactor 22A in lead mode to oligomerize the charge olefin stream over the upstream first, first stage oligomerization catalyst bed 22a to produce an upstream first oligomerized olefin stream. The corresponding valves on connecting lines 121 to the second reactor 22B and 122 to the third reactor 22C in downstream communication with line 20a are closed in this mode. The upstream first, first stage oligomerization catalyst bed 22a of the first reactor 22A formerly underwent regeneration in regeneration mode. The upstream first, first stage oligomerization catalyst bed 22a of the first reactor 22A may have previously oligomerized the charged olefin stream in the lag mode to produce an upstream second oligomerized olefin stream prior to regeneration. The upstream first oligomerized olefin stream is discharged in the upstream first oligomerized effluent line 24a through an open valve on tie line 124 from the upstream first, first stage oligomerization catalyst bed 22a and is transported to line 12b and the second charge cooler18b depicted in FIG. 1. The corresponding valves on tie lines 125 and 126 from the second reactor 22B and the third reactor 22C in upstream communication with the line 24a are closed in this mode.

The second cooled diluted olefin stream in line 20b from FIG. 1 through an open valve on tie line 130 is charged to the downstream first, first stage oligomerization catalyst bed 22b in lead mode to oligomerize the charged olefin stream over the downstream first, first stage oligomerization catalyst bed to produce a downstream first oligomerized olefin stream. The corresponding valves on tie line 131 to the second reactor 22B and on tie line 132 to the third reactor 22C in downstream communication with line 20b are closed in this mode. The downstream first, first stage oligomerization catalyst bed of first reactor 22A formerly underwent regeneration in regeneration mode. The downstream first, first stage oligomerization catalyst bed 22b of first reactor 22A may have previously oligomerized the charged olefin stream in lag mode to produce an upstream second oligomerized olefin stream prior to regeneration. The downstream first oligomerized olefin stream is discharged from the downstream first, first stage oligomerization catalyst bed 22b in the downstream first oligomerized effluent line 24b through an open valve on a tie line 135 and transported to line 12c and to the third charge the cooler 18c in FIG. 1 for the second reactor 22B. The corresponding valves on the tie lines 136 and 137 for the second reactor 22B and the third reactor 22C, respectively, in upstream communication with line 24b are closed when the first reactor 22A is in lead mode.

Line 20c of FIG. 1 charges the third cooled diluted olefin stream through an open valve on a connecting line 141 to the upstream second, first stage oligomerization catalyst bed 22c of the second reactor 22B in lag mode to oligomerize the charged olefin stream over the upstream second, first stage oligomerization catalyst bed to produce an upstream second oligomerized olefin stream. The corresponding valves on connecting lines 140 to the first reactor 22A and 142 to the third reactor 22C in downstream communication with line 20c are closed in this mode. The upstream second, first stage oligomerization catalyst bed 22c of the second reactor 22B formerly underwent regeneration in regeneration mode. The upstream second, first stage oligomerization catalyst bed 22c of the second reactor 22B may have previously oligomerized the charged olefin stream in the lead mode to produce an upstream second oligomerized olefin stream after regeneration. The upstream second oligomerized olefin stream is discharged in the upstream second oligomerized effluent line 24c through an open valve on tie line 145 from the upstream second, first stage oligomerization catalyst bed 22c and is transported to line 12d and the fourth charge cooler18d depicted in FIG. 1. The corresponding valves on tie lines 144 and 146 from the second reactor 22B and the third reactor 22C, respectively, in upstream communication with line 24a are closed in this mode.

The fourth cooled diluted olefin stream in line 20d from FIG. 1 through an open valve on tie line 151 is charged to the downstream second, first stage oligomerization catalyst bed 22d in lag mode to oligomerize the charged olefin stream over the downstream second, first stage oligomerization catalyst bed to produce a downstream second oligomerized olefin stream. The corresponding valves on tie line 150 to the first reactor 22A and on tie line 152 to the third reactor 22C in downstream communication with line 20d are closed in this mode. The downstream second, first stage oligomerization catalyst bed 22d of the second reactor 22B formerly underwent regeneration in regeneration mode. The downstream second, first stage oligomerization catalyst bed 22d of second reactor 22B may have previously oligomerized the charged olefin stream in lead mode to produce an upstream second oligomerized olefin stream after regeneration. The downstream second oligomerized olefin stream is discharged from the downstream second, first stage oligomerization catalyst bed 22d in the downstream second oligomerized effluent line 24d through an open valve on a tie line 156 and transported to the cooler 27 in FIG. 1. The corresponding valves on the tie lines 155 and 157 for the first reactor 22A and the third reactor 22C, respectively, in upstream communication with line 24d are closed when the second reactor 22B is in lead mode.

After the upstream first, first stage oligomerization catalyst bed 22a and the downstream first, first stage oligomerization catalyst bed 22b in the first reactor 22A are spent in lead mode, charge of the olefin stream to the respective beds may be discontinued and regeneration may begin. Alternatively, after the upstream second, first stage oligomerization catalyst bed 22c and the downstream second, first stage oligomerization catalyst bed 22d of the second reactor 22B in lag mode are spent, charge of the olefin stream to the upstream first, first stage oligomerization catalyst bed 22a and the downstream first, first stage oligomerization catalyst bed 22b in the first reactor 22A may be continued but in lag mode while the second reactor 22B is move to regeneration mode.

In FIG. 3, the third reactor is in regeneration mode. Line 100 charges a stream of regeneration gas to an upstream third, first stage oligomerization catalyst bed 22e of the third, first stage reactor 22C in regeneration mode through a tie line 162 and an open valve thereon. The corresponding valves on tie line 160 to the first, first stage reactor 22A in lead mode and on tie line 161 to the second, first stage reactor 22B in lag mode in downstream communication with line 100 are closed. The regeneration gas may comprise oxygen and be at elevated temperature. The upstream third, first stage oligomerization catalyst bed 22e was formerly in the lead mode and alternatively most immediately formerly in the lag mode. The regeneration gas from the upstream third, first stage oligomerization catalyst bed 22e may be fed through an open valve on line 102c to the downstream third, first stage oligomerization catalyst bed 22f to regenerate the catalyst therein. Corresponding valves on lines 102a and 102b on the first, first stage reactor 22A and the second, first stage reactor 22B in downstream communication with the upstream first stage catalyst bed 22a and 22b are closed. Regeneration flue gas exits the downstream third, first stage oligomerization catalyst bed 22f in tie line 167 with an open valve thereon and is discharged in line 106. Corresponding valves on tie line 165 for the first, first stage reactor 22A and on tie line 166 for the second, first stage reactor 22B in upstream communication with line 106 are closed when the third reactor 22C is in regeneration mode. After regeneration, the third reactor 22C may move from the regeneration reactor to the lead reactor while the first reactor 22A moves from the lead to the lag reactor and the second reactor 22B enters the regeneration mode from lag mode.

Figure 4:
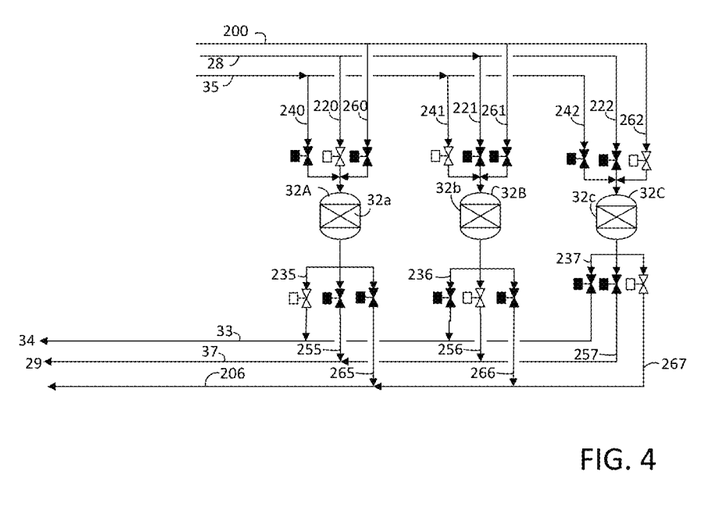
FIG. 4 is an additional schematic drawing of a regeneration process for the oligomerization section of a process and apparatus of the present disclosure.

FIG. 4 illustrates a process for regeneration of the second stage oligomerization reactors 32. The regeneration process may utilize three second stage oligomerization reactors 32, first reactor 32A, a second reactor 32B and a third reactor 32C. The three reactors switch between lead, lag and regeneration mode. In FIG. 4, the first reactor 32A is in lead mode, the second reactor 32B is in lag mode and the third reactor 32C is in regeneration mode. FIG. 4 relates to FIG. 1. In FIG. 4, unfilled valves are open and filled valves are closed. Furthermore, capital letters in the reference characters are distinct from lower case letters.

Line 28 of FIG. 1 charges a cooled oligomerized olefin stream through an open valve on a connecting line 220 to the first, second stage oligomerization catalyst bed 32a of the first, second stage reactor 32A in lead mode to oligomerize the oligomerized olefin stream over the first, second stage oligomerization catalyst bed 32a to produce a first oligomerate stream. The corresponding valves on connecting lines 221 to the second, second stage reactor 32B and 222 to the third reactor 32C in downstream communication with line 28 are closed in this mode. The first, second stage oligomerization catalyst bed 32a of the first reactor 32A formerly underwent regeneration in regeneration mode. The first, second stage oligomerization catalyst bed 32a of the first reactor 32A may have previously oligomerized the charged olefin stream in the lag mode to produce a second oligomerate stream prior to regeneration. The first oligomerate stream is discharged in the first oligomerate line 33 through an open valve on connecting line 235 from the first, second stage oligomerization catalyst bed 32a and is transported in line 33 to the second charge cooler 34 depicted in FIG. 1. The corresponding valves on connecting lines 236 and 237 from the second reactor 32B and the third reactor 32C in upstream communication with line 33, respectively, are closed in this mode.

The first cooled oligomerate stream in line 35 from FIG. 1 through an open valve on connecting line 241 is charged to the second, second stage oligomerization catalyst bed 32b in the second, second stage oligomerization catalyst bed 32b in lag mode to oligomerize the oligomerate stream over the second, second stage oligomerization catalyst bed to produce a second oligomerate stream. The corresponding valves on connecting line 240 to the first 32A and on connecting line 242 to the third reactor 32C in downstream communication with line 35 are closed in this mode. The second, second stage oligomerization catalyst bed of second, second stage reactor 32B formerly underwent regeneration in regeneration mode. The second, second stage oligomerization catalyst bed 32b of the second reactor 32A may have previously oligomerized the oligomerate stream in lead mode to produce a first oligomerate stream after regeneration. The second oligomerate stream is discharged from the second, second stage oligomerization catalyst bed 32b in the second, second stage reactor 32B through an open valve on a connecting line 256 and transported in the second oligomerate line 37 to the heat exchanger 29 in FIG. 1 eventually to fractionation in the olefin splitter column 36. The corresponding valves on the tie lines 255 and 257 for the first, second stage reactor 32A and the third, second stage reactor 32C, respectively, in upstream communication with line 37 are closed when the second reactor 32B is in lag mode.

After the first, second stage oligomerization catalyst bed 32a in the first, second stage reactor 32A is spent in lead mode, charge of the oligomerate stream to the first, second stage oligomerization reactor may be discontinued, and regeneration may begin. Alternatively, after the second, second stage oligomerization catalyst bed 32b of the second, second stage reactor 32B in lag mode is spent, charge of the oligomerate stream to the first, second stage oligomerization catalyst bed 32a in the first, second stage reactor 32A may be continued but in lag mode while the second, second stage reactor 32B is moved to regeneration mode.

In FIG. 4, the third reactor 32C is in regeneration mode. Line 200 charges a stream of regeneration gas to a third, second stage oligomerization catalyst bed 32c of the third, second stage reactor 32C in regeneration mode through a connecting line 262 and an open valve thereon. The corresponding valves on connecting line 260 to the first, second stage reactor 32A in lead mode and on the connecting line 261 to the second, second stage reactor 22B in lag mode in downstream communication with line 200 are closed. The regeneration gas may comprise oxygen and be at elevated temperature. The third, second stage oligomerization catalyst bed 32c was formerly in the lead mode and alternatively most immediately formerly in the lag mode before regeneration mode. Regeneration flue gas exits the downstream third, second stage oligomerization catalyst bed 32c in connecting line 267 with an open valve thereon and is discharged in line 206. Corresponding valves on tie line 265 for the first, second stage reactor 32A and on tie line 266 for the second, second stage reactor 32B in upstream communication with line 206 are closed when the third reactor 32C is in regeneration mode. After regeneration, the third reactor 32C may move from the regeneration reactor to the lead reactor while the first reactor 32A may move from the lead reactor to the lag reactor and the second reactor 22B moves from lag reactor to regeneration mode.

Figure 5:
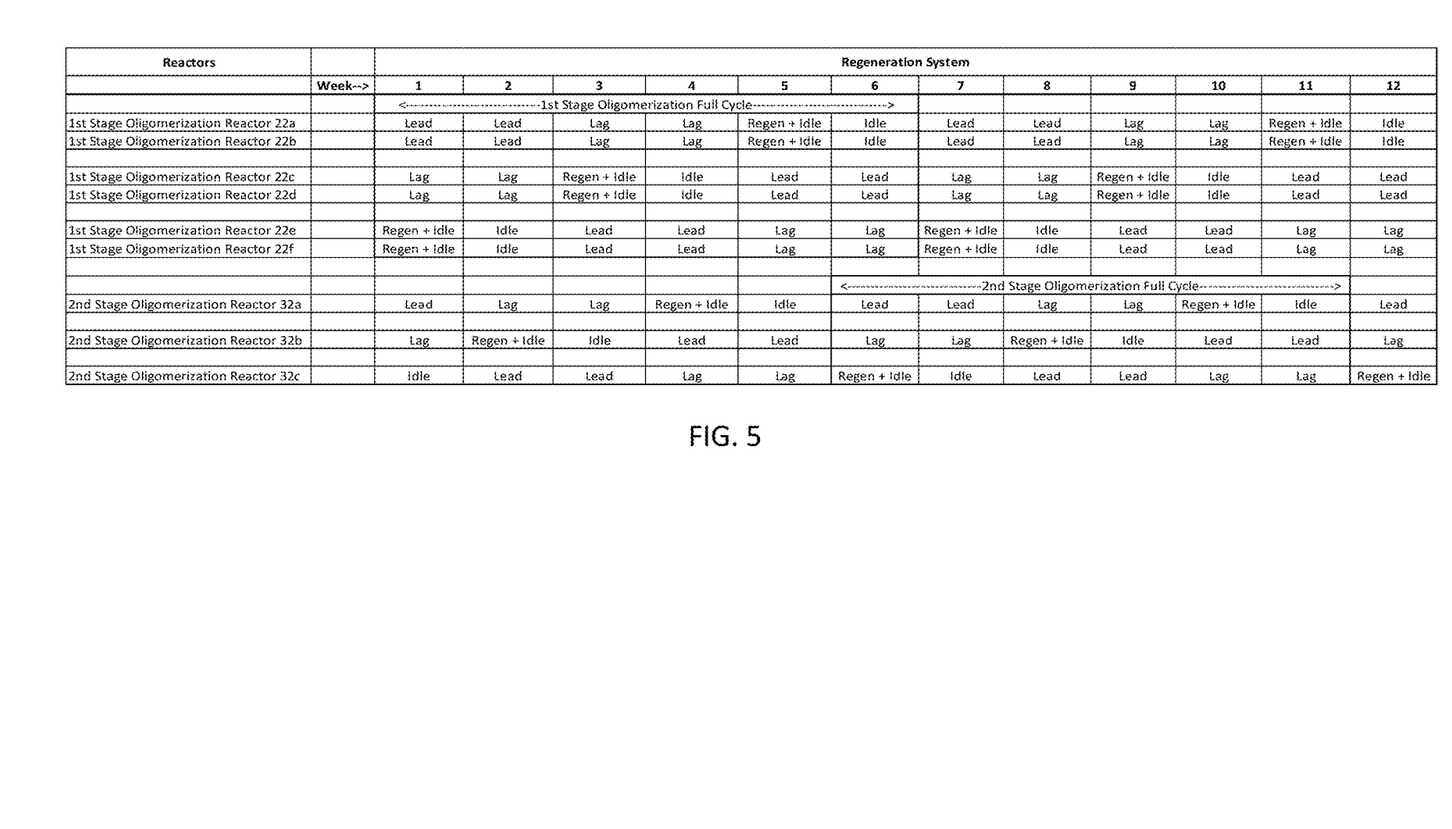
FIG. 5 is a table of a continuous operation and regeneration schedule of the present disclosure.

In order to allow for one regeneration system to regenerate each catalyst within a two-week period, a scheduling system has been developed which is shown in FIG. 5 to accommodate requirements for regeneration timing and still allow for some flexibility in scheduling with down time planned. Regeneration may occur no more than twice per month per reactor, more preferably no more than once per month per reactor or more preferably no more than once every 5 weeks per reactor.

EXAMPLES

Example 1

Spent first stage oligomerization MTT zeolite catalyst and second stage oligomerization nickel on amorphous silica alumina catalyst from a first pilot plant cycle test contacted in a stacked bed configuration with ethylene feed and light paraffin diluent were regenerated ex-situ. The regeneration procedure consisted of a high temperature nitrogen purge at 400° C., at 600-800 h$^{-1}$ gas hourly space velocity, followed by coke burn at 450° C. in a controlled $O_2$ environment of 2 wt % and 7 wt % $O_2$ in $N_2$ and proof coke burn in 18 wt % $O_2$ in $N_2$. As shown in Table 1, the 400° C. nitrogen purge removed significant amounts of carbonaceous species. Based on gas chromatography analysis, the purged hydrocarbon species are C8-C20 olefins. The carbon burn step removed completely the coke on the second stage Ni/ASA catalyst, however, the regenerated first stage zeolite MTT catalyst contains approximately 1 wt % hard-to-burn coke. As demonstrated experimentally, the hard-to-burn coke on the first stage oligomerization catalyst does not negatively impact the catalyst performance. The hard-to-burn coke remains at the same level after consecutive regenerations in all subsequent cycles and does not accumulate beyond 1 wt %.

TABLE 1

Carbon, hydrogen and nitrogen analysis for spent and hot nitrogen purged $1^{st}$ stage and $2^{nd}$ stage oligomerization catalysts.

| Catalyst Description | Spent 1st Stage MTT zeolite catalyst | Spent 2nd stage Ni/ASA catalyst | 1st stage MTT zeolite catalyst after 400° C. N2 Purge | 2nd stage Ni/ASA Catalyst after 400° C. N2 purge | Regenerated 1st stage MTT zeolite catalyst after C burn | Regenerated 2nd stage Ni/ASA catalyst after C burn |
|---|---|---|---|---|---|---|
| C, wt % | 5.0 | 10.5 | 1.3 | 0.7 | 0.9 | 0.1 |
| H, wt % | 1.05 | 1.87 | 0.49 | 0.38 | 0.75 | 0.66 |
| N, wt % | 0.06 | <0.05 | <0.05 | <0.05 | <0.05 | <0.05 |

Example 2

Pilot plant tests with both a first stage oligomerization catalyst comprising MTT zeolite and a second stage oligomerization catalysts comprising nickel on amorphous silica alumina confirmed two weeks or longer operation providing satisfactory conversion at acceptable temperatures in a first cycle with complete performance recovery in the second cycle after ex-situ regeneration.

Figure 6:
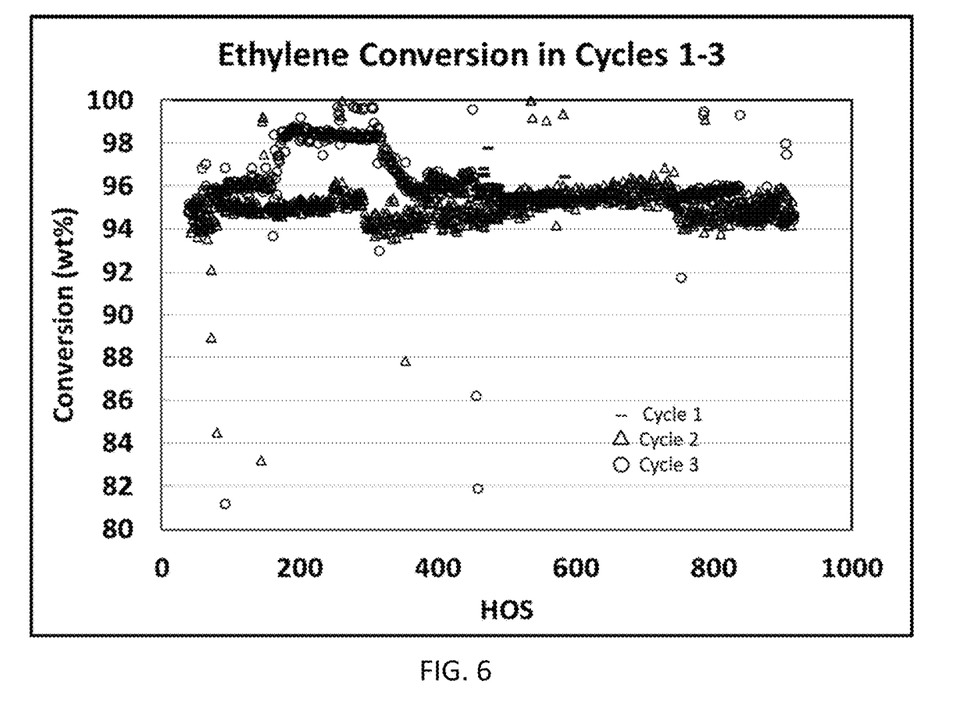
FIG. 6 is a plot of conversion over time before and after regeneration.

FIG. 6 shows ethylene conversion over time for three cycles. The first cycle is with fresh MTT zeolite catalyst and nickel on amorphous silica alumina catalyst arranged in a stacked bed configuration in the pilot plant reactor indicated by the dashes. The second cycle in triangles and the third cycle in circles represent conversion over regenerated catalysts. The regenerated cycles have comparable conversion to fresh catalysts before any regeneration.

Figure 7:
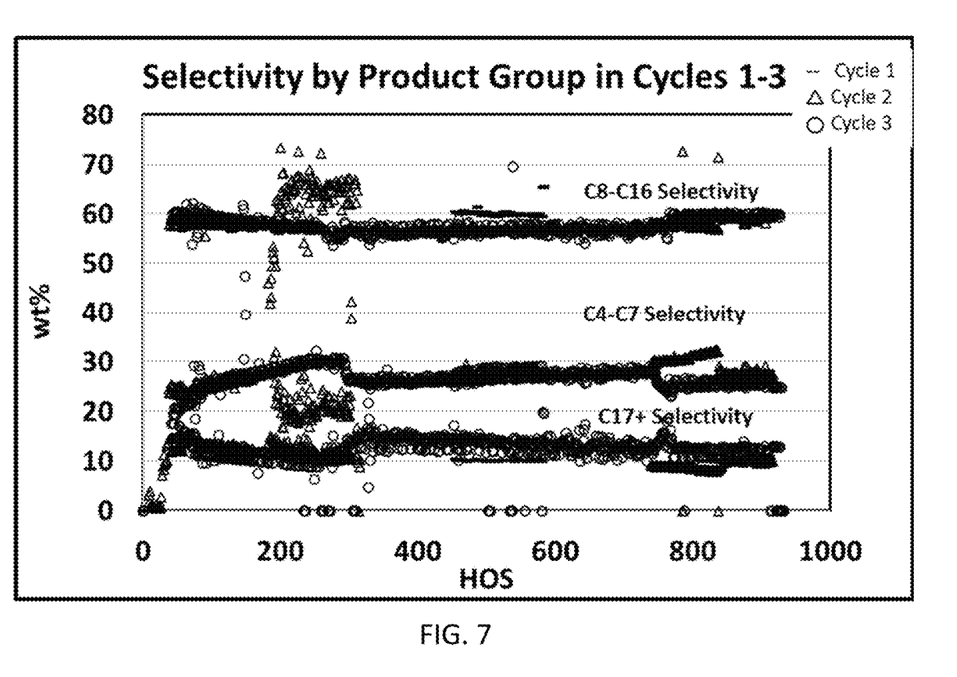
FIG. 7 is a plot of selectivity over time before and after regeneration.

FIG. 7 shows oligomer selectivity over time for three cycles. Again, the first cycle is with fresh MTT zeolite catalyst and nickel on amorphous silica alumina catalyst arranged in a stacked bed configuration in the pilot plant reactor indicated by the dashes. The second cycle in triangles and the third cycle in circles represent conversion over regenerated catalysts. The regenerated cycles have comparable selectivities to fresh catalysts before any regeneration.

SPECIFIC EMBODIMENTS

While the following is described in conjunction with specific embodiments, it will be understood that this description is intended to illustrate and not limit the scope of the preceding description and the appended claims.

A first embodiment of the disclosure is a process for oligomerizing an olefin stream comprising oligomerizing a charge olefin stream over a first, first stage oligomerization catalyst bed to produce a first oligomerized olefin stream; regenerating the first oligomerization catalyst bed; oligomerizing the charge olefin stream over a second, first stage oligomerization catalyst bed to produce a second oligomerized olefin stream; oligomerizing the charge olefin stream over the first, first stage oligomerization catalyst bed to produce the first oligomerized olefin stream. An embodiment of the disclosure is one, any or all of prior embodiments in this paragraph up through the first embodiment in this paragraph further comprising regenerating the second oligomerization catalyst bed. An embodiment of the disclosure is one, any or all of prior embodiments in this paragraph up through the first embodiment in this paragraph further comprising regenerating the first, first stage oligomerization catalyst bed by feeding an oxygen gas to the catalyst bed at elevated temperature. An embodiment of the disclosure is one, any or all of prior embodiments in this paragraph up through the first embodiment in this paragraph further comprising oligomerizing the charge olefin stream over a third, first stage oligomerization catalyst bed to produce an oligomerized olefin stream. An embodiment of the disclosure is one, any or all of prior embodiments in this paragraph up through the first embodiment in this paragraph further comprising discontinuing oligomerizing the charge olefin stream over the first, first stage oligomerization catalyst bed before regenerating the first, first stage oligomerization catalyst bed. An embodiment of the disclosure is one, any or all of prior embodiments in this paragraph up through the first embodiment in this paragraph further comprising discontinuing oligomerizing the charge olefin stream over the second, first stage oligomerization catalyst bed before regenerating the second, first stage oligomerization catalyst bed. An embodiment of the disclosure is one, any or all of prior embodiments in this paragraph up through the first embodiment in this paragraph further comprising oligomerizing an oligomerized olefin stream over a first, second stage oligomerization catalyst bed to produce a first oligomerate stream; regenerating the first, second stage oligomerization catalyst bed; and oligomerizing the oligomerized olefin stream over a second, second stage oligomerization catalyst bed to produce a second oligomerate stream. An embodiment of the disclosure is one, any or all of prior embodiments in this paragraph up through the first embodiment in this paragraph further comprising regenerating the second, second stage oligomerization catalyst bed. An embodiment of the disclosure is one, any or all of prior embodiments in this paragraph up through the first embodiment in this paragraph further comprising regenerating the first, second stage oligomerization catalyst bed by feeding an oxygen gas to the catalyst bed at elevated temperature. An embodiment of the disclosure is one, any or all of prior embodiments in this paragraph up through the first embodiment in this paragraph further comprising regenerating said first, second stage oligomerization catalyst bed while oligomerizing said oligomerized olefin stream over said second, second stage oligomerization catalyst bed. An embodiment of the disclosure is one, any or all of prior embodiments in this paragraph up through the first embodiment in this paragraph comprising oligomerizing a charge olefin stream over first stage oligomerization catalyst continuously for at least a month. An embodiment of the disclosure is one, any or all of prior embodiments in this paragraph up through the first embodiment in this paragraph further comprising oligomerizing the oligomerized olefin stream over second stage oligomerization catalyst continuously for at least two weeks.

A second embodiment of the disclosure is a process for oligomerizing an olefin stream comprising oligomerizing a charge olefin stream over a first, first stage oligomerization catalyst bed to produce a first oligomerized olefin stream;

oligomerizing the first oligomerized olefin stream over a first, second stage oligomerization catalyst bed to produce a first oligomerate stream; regenerating the first, second stage oligomerization catalyst bed; and oligomerizing the first oligomerized olefin stream over a second, second stage oligomerization catalyst bed to produce a second oligomerate stream. An embodiment of the disclosure is one, any or all of prior embodiments in this paragraph up through the second embodiment in this paragraph further comprising regenerating the second, second stage oligomerization catalyst bed. An embodiment of the disclosure is one, any or all of prior embodiments in this paragraph up through the second embodiment in this paragraph further comprising regenerating the first, second stage oligomerization catalyst bed by feeding an oxygen gas to the catalyst bed at elevated temperature. An embodiment of the disclosure is one, any or all of prior embodiments in this paragraph up through the second embodiment in this paragraph further comprising discontinuing oligomerizing the oligomerized olefin stream over the first, second stage oligomerization catalyst bed before regenerating the first, second stage oligomerization catalyst bed. An embodiment of the disclosure is one, any or all of prior embodiments in this paragraph up through the second embodiment in this paragraph further comprising discontinuing oligomerizing the oligomerized olefin stream over the second, second stage oligomerization catalyst bed before regenerating the second, second stage oligomerization catalyst bed. An embodiment of the disclosure is one, any or all of prior embodiments in this paragraph up through the second embodiment in this paragraph further comprising oligomerizing the oligomerized olefin stream over second stage oligomerization catalyst continuously for at least two weeks.

A third embodiment of the disclosure is a process for oligomerizing an olefin stream comprising oligomerizing a charge olefin stream over a first, first stage oligomerization catalyst bed to produce a first oligomerized olefin stream; regenerating the first oligomerization catalyst bed; oligomerizing the charge olefin stream over a second, first stage oligomerization catalyst bed to produce a second oligomerized olefin stream; oligomerizing the first oligomerized olefin stream or the second oligomerized olefin stream over a first, second stage oligomerization catalyst bed to produce a first oligomerate stream; regenerating the first, second stage oligomerization catalyst bed; oligomerizing the first oligomerized olefin stream or the second oligomerized olefin stream over a second, second stage oligomerization catalyst bed to produce a second oligomerate stream. An embodiment of the disclosure is one, any or all of prior embodiments in this paragraph up through the third embodiment in this paragraph further comprising discontinuing oligomerizing the charge olefin stream over the first, first stage oligomerization catalyst bed before regenerating the first, first stage oligomerization catalyst bed.

Without further elaboration, it is believed that using the preceding description that one skilled in the art can utilize the present disclosure to its fullest extent and easily ascertain the essential characteristics of this disclosure, without departing from the spirit and scope thereof, to make various changes and modifications of the disclosure and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for oligomerizing an olefin stream comprising:
   oligomerizing a charge olefin stream over a first, first stage oligomerization catalyst bed to produce a first oligomerized olefin stream;
   regenerating said first, first stage oligomerization catalyst bed;
   oligomerizing said charge olefin stream over a second, first stage oligomerization catalyst bed to produce a second oligomerized olefin stream;
   oligomerizing said charge olefin stream over said first, first stage oligomerization catalyst bed to produce said first oligomerized olefin stream.

2. The process of claim 1 further comprising regenerating said second, first stage oligomerization catalyst bed.

3. The process of claim 1 further comprising regenerating said first, first stage oligomerization catalyst bed by feeding an oxygen gas to the first, first stage oligomerization catalyst bed at elevated temperature.

4. The process of claim 1 further comprising oligomerizing said charge olefin stream over a third, first stage oligomerization catalyst bed to produce an oligomerized olefin stream.

5. The process of claim 1 further comprising discontinuing oligomerizing said charge olefin stream over said first, first stage oligomerization catalyst bed before regenerating said first, first stage oligomerization catalyst bed.

6. The process of claim 1 further comprising discontinuing oligomerizing said charge olefin stream over said second, first stage oligomerization catalyst bed before regenerating said second, first stage oligomerization catalyst bed.

7. The process of claim 1 further comprising regenerating said first, first stage oligomerization catalyst bed by feeding an inert gas, a hydrocarbon, or a solvent to the catalyst bed at elevated temperature.

8. The process of claim 7 further comprising feeding an oxygen gas to the catalyst bed at elevated temperature.

9. The process of claim 1 further comprising:
   oligomerizing an oligomerized olefin stream over a first, second stage oligomerization catalyst bed to produce a first oligomerate stream;
   regenerating said first, second stage oligomerization catalyst bed;
   oligomerizing said oligomerized olefin stream over a second, second stage oligomerization catalyst bed to produce a second oligomerate stream.

10. The process of claim 9 further comprising regenerating said second, second stage oligomerization catalyst bed.

11. The process of claim 9 further comprising regenerating said first, second stage oligomerization catalyst bed by feeding an oxygen gas to the first, first stage oligomerization catalyst bed at elevated temperature.

12. The process of claim 9 further comprising regenerating said first, second stage oligomerization catalyst bed while oligomerizing said oligomerized olefin stream over said second, second stage oligomerization catalyst bed.

13. The process of claim 1 comprising oligomerizing a charge olefin stream over said first, first stage oligomerization catalyst continuously for at least two weeks.

14. The process of claim 9 further comprising oligomerizing said oligomerized olefin stream over first, second stage oligomerization catalyst continuously for at least two weeks.

15. A process for oligomerizing an olefin stream comprising:
oligomerizing a charge olefin stream over a first, first stage oligomerization catalyst bed to produce a first oligomerized olefin stream;
oligomerizing said first oligomerized olefin stream over a first, second stage oligomerization catalyst bed to produce a first oligomerate stream;
regenerating said first, second stage oligomerization catalyst bed; and
oligomerizing said first oligomerized olefin stream over a second, second stage oligomerization catalyst bed to produce a second oligomerate stream.

16. The process of claim 15 further comprising regenerating said second, second stage oligomerization catalyst bed.

17. The process of claim 15 further comprising regenerating said first, second stage oligomerization catalyst bed by feeding an inert gas, a hydrocarbon, or a solvent to the first, second stage oligomerization catalyst bed at elevated temperature and feeding an oxygen gas to the first, second stage oligomerization catalyst bed at elevated temperature.

18. The process of claim 15 further comprising discontinuing oligomerizing said oligomerized olefin stream over said first, second stage oligomerization catalyst bed before regenerating said first, second stage oligomerization catalyst bed.

19. The process of claim 16 further comprising discontinuing oligomerizing said oligomerized olefin stream over said second, second stage oligomerization catalyst bed before regenerating said second, second stage oligomerization catalyst bed.

20. A process for oligomerizing an olefin stream comprising:
oligomerizing a charge olefin stream over a first, first stage oligomerization catalyst bed to produce a first oligomerized olefin stream;
regenerating said first, first stage oligomerization catalyst bed;
oligomerizing said charge olefin stream over a second, first stage oligomerization catalyst bed to produce a second oligomerized olefin stream;
oligomerizing said first oligomerized olefin stream or said second oligomerized olefin stream over a first, second stage oligomerization catalyst bed to produce a first oligomerate stream;
regenerating said first, second stage oligomerization catalyst bed;
oligomerizing said first oligomerized olefin stream or said second oligomerized olefin stream over a second, second stage oligomerization catalyst bed to produce a second oligomerate stream.

* * * * *